United States Patent [19]
Howell

[11] 3,949,745
[45] Apr. 13, 1976

[54] PARENTERAL FLUID ADMINISTRATION SET

[76] Inventor: William L. Howell, 3615 Macomb St., N.W., Washington, D.C. 20016

[22] Filed: Aug. 28, 1975

[21] Appl. No.: 608,576

[52] U.S. Cl............. 128/214 C; 128/228; 137/135; 222/416
[51] Int. Cl.² ......................................... A61M 5/16
[58] Field of Search ......... 128/214 R, 214 C, 214.2, 128/227, 228; 137/123, 130, 131, 135, 142, 149, 150, 152, 153, 578; 222/67, 204, 416

[56] References Cited
UNITED STATES PATENTS

| | | | |
|---|---|---|---|
| 736,516 | 8/1903 | Griffiths | 137/135 |
| 2,090,273 | 8/1937 | Wagner | 137/399 |
| 2,542,461 | 2/1951 | Bay | 128/228 |
| 2,640,358 | 2/1953 | McClure | 222/416 X |
| 2,648,333 | 8/1953 | Cutter | 128/214 C |
| 3,160,330 | 12/1964 | Pollitt | 222/416 |
| 3,667,464 | 6/1972 | Alligood | 128/214 C |

FOREIGN PATENTS OR APPLICATIONS

| | | | |
|---|---|---|---|
| 21,724 | 9/1947 | Finland | 137/135 |

*Primary Examiner*—Dalton L. Truluck
*Attorney, Agent, or Firm*—J. Harold Kilcoyne

[57] ABSTRACT

A device for administering parenteral fluids intravenously at a uniform rate achieved by a floating siphon-type flow regulating means.

10 Claims, 4 Drawing Figures

U.S. Patent  April 13, 1976  3,949,745
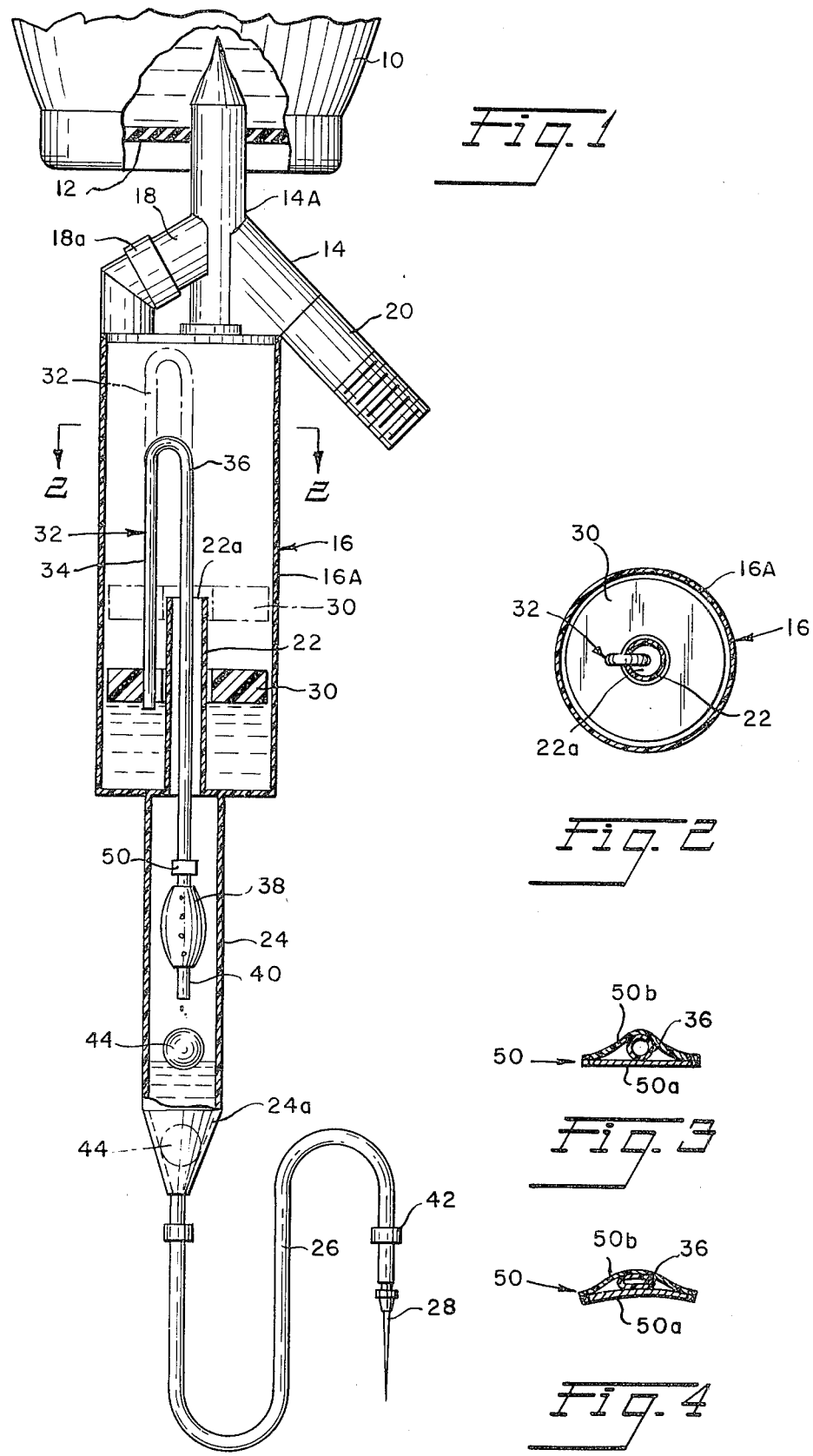

3,949,745

PARENTERAL FLUID ADMINISTRATION SET

THE INVENTION

The present invention relates to a device for the administration of parenteral fluids intravenously and more particularly to such a device characterized by a floating-siphon type of flow regulator which insures flow of a parenteral fluid being administered at a controllable uniform rate.

BACKGROUND OF THE INVENTION

Parenteral fluids are usually given in aliquots of 500–1,000 cc at room temperature and desirably at a uniform rate of flow, but current means and/or procedures for insuring uniform rate of flow require electrically-powered positive-pressure pumps which are both expensive and cumbersome in use, the latter because patients being infused often must be moved about, to an X-ray room for example, such necessitating disconnection of the pump motor, with the result that flow of the fluid be stopped until another electrical connection is reached. In orther situations, it is desirable that patients be ambulatory, i.e. walking halls, etc., as when receiving heparin, with the result that the patients' walking is restricted to an area limited by the radius provided by the extension cord.

While various attempts have been made previously to devise a more simple and less cumbersome means for uniform flow administration of parenteral fluids (one such being the subject of Bay U.S. Pat. No. 2,542,461 dated Feb. 20, 1951 which uses a fixed siphon and another being the subject of patent to Fernandez U.S. Pat. No. 2,850,211 employing a float which rides on the surface of the fluid in an inverted bottle-type of reservoir, none has proved acceptable in practice, with the result that uniformity of flow is usually attempted by frequent visits of nurses to the administration set to count the number of drops per minute or by the rate of emptying of a small reservoir made a part of the intravenous tubing.

OBJECTS OF THE INVENTION

The present invention aims to provide (and provides) a simple yet highly effective device for administering parenteral fluids intravenously at a uniform rate achieved by means of a floating siphon-type flow regulator which, when made operative (primed) maintains constant (a) the vertical distance between the siphon intake and the surface of a body of the fluid supplied to a flow regulator on which the siphon floats, and (b) the vertical distance between siphon intake and outlet. Such a siphon once filled and made operative will maintain uniform flow modified only (1) by change in fluid viscosity; (2) by the alteration of the calibre (bore) of the siphon; and (3) by atmospheric pressure which latter for all practical purposes can be disregarded.

The invention also aims to provide (and provides) simple means for altering the calibre of the siphon at a point along the length of the flow path therethrough near the siphon outlet, in accordance with the viscosity of the particular fluids being administered intravenously and/or the condition or need of the patient being treated.

The above and other objects and features of advantage of a device for the administration of parenteral fluids intravenously employing a floating siphon-type flow regulating means will appear from the accompanying drawings and following description thereof, wherein …… .

FIG. 1 is a vertical sectional view (in part-elevation) illustrating the device of the invention on an enlarged scale coupled in operative association to a bottle-type reservoir of an intravenous fluid to be administered, the view illustrating in broken lines the floating siphon in its approximate uppermost position as determined by the open top of an overflow tube.

FIG. 2 is a section through the flow regulator taken on a horizontal plane 2—2;

FIGS. 3 and 4 are detail views illustrating a preferred form of a clamp (and the positioning thereof) functioning to vary the calibre of the siphon in accordance with the viscosity of the fluid being administered and/or the condition or requirements of the patient;

Referring now to the drawing figures in detail, reference numeral 10 (FIG. 1) designates the neck end of an intravenous fluid supply i.e. a reservoir-bottle mounted (usually suspended) in inverted position and with its neck opening capped as by a cap 12 but with said cap shown to have been pierced by the point of a tubular needle-like member 14A of a conventional fixture or adapter 14, incorporating a fluid-flow outlet leg 18 through the bore of which fluid from the bottle may flow to the interior of a flow regulator generally designated 16, upon opening of a valve 18a in said fluid outlet leg 18 air being meanwhile supplied to the bottle interior and permitted to vent from the flow regulator chamber through filtered air inlet and vent openings (not shown) usually incorporated in the air supply and venting leg 20 of said fixture.

Illustratively, the flow regulator 16 comprises a clear plastic, uprightly disposed cylindrical fluid container 16A to whose upper end the aforesaid fixture or adapter 14 is fitted so that it serves as an upper-end container closure, and from whose bottom end wall extends an upright open-top tube 22 functioning as an overflow tube or pipe. Thus, fluid may collect in the lower portion of the cylindrical container 16A until it reaches the level of the open top 22a of said tube 22, whereupon any overflow passes downwardly through the tube to a lower-level elongate receiving reservoir 24 shown to have substantially less diameter than that of the container 16A from which it depends. Illustratively, said receiving reservoir 24 is disposed in coaxial relation with both said container 16A and the uprightly disposed overflow tube 22 therein and terminates at its lower end in a tapering end portion 24a delivering to the intravenous tubing 26 which in turn terminates in an injection needle 28.

Disposed within the upright cylindrical container member 16A is an annular float member 30, through the central aperture having diameter slightly greater than that of and through which the aforesaid overflow tube 22 extends, said float thus riding on the surface of any substantial body of intravenous fluid collecting in the lower end of the container 16A, to an uppermost position determined by the fluid level reaching that of the upper open end 22a of said overflow tube 22.

According to a further important and unique feature of the present invention, said float 30 so mounts the inverted U-tube of a siphon generally designated 32 that both move as one within the limits of float motion. More particularly, the shorter leg 34 of the siphon 32 extends downwardly through the float 30, being fixedly secured thereto in position such that its lower intake end is always submerged in the fluid on which said float rides, as above. As distinguished therefrom, the longer leg 36 of the siphon extends from the U-bend thereof downwardly through the upright overflow tube 22 (whose internal diameter is such as to permit free motion of said leg with said float) into the interior space of the receiving reservoir 24 and terminates in a priming bulb 38, the latter having a short length 40 of tubing extending downwardly therefrom.

Further unique features of the invention are that the receiving reservoir 24, the longer leg 36 of the siphon 32 or at least the length portion thereof disposed just above the priming bulb 38, said priming bulb and the short length of tubing 40 extending downwardly from the latter, are each fashioned from a pliable plastic material which readily deforms by hand-squeeze pressure or finger-squeeze applied thereto but which is capable of reforming to original shape following any such deformation. Thus, the priming bulb 38 may be squeezed substantially flat by hand pressure when priming of the siphon is desired. Similarly, the bore of the short length of tubing 40 depending therefrom may be closed as by pinching said tubing between thumb and forefinger, all as made possible by the deformability of the plastic material from which said parts (and the wall of the receiving reservoir 24 as well) are fashioned, and upon such priming and upon pinching of the short length of tubing 40 having been accomplished, the capability thereof to re-form to their original shape.

Such is a feature of advantage as it provides means for aseptically priming the siphon.

It is also explained that a sphere 44 of floatable material capable of functioning as a floating ball valve is preferably contained in the lower tapering portion 24a of the fluid-receiving reservoir 24, such sphere riding on any substantial body of fluid collecting in said lower tapering end. It will be appreciated that the action of said floating sphere is that of being capable, upon the body of fluid having discharged therefrom, of lowering to a position in which it functions to close off entry of air to the interior of said receiving reservoir through the lower end thereof.

Without further analysis, it will be appreciated that the above described device provides for a uniform rate of flow of parenteral fluids intravenously and that such is accomplished principally by means of a floating siphon 32 which maintains constant (*a*) the vertical distance between the siphon intake, i.e. the lower open end of the shorter leg 34 of said siphon which projects downwardly through the float 30, and the surface of the fluid collecting in the flow-regulator container 16A; and (*b*) the vertical distance between said siphon intake and the siphon outlet which for all practical purposes is a point along the length of the longer siphon leg just above the priming bulb 38. Such a siphon, once suitably primed and rendered operative, will maintain constant uniform flow, modified only by (1) a change in the viscosity of the intravenous fluid being administered and/or (2) in the calibre (bore) of the siphon tubes or legs.

Referring to FIGS. 3 and 4, such illustrate a simple effective clamp means generally designated 50 functioning to alter the calibre of the siphon bore and thereby the rate of flow of fluid through the siphon in accordance with the viscosity of the fluid being administered and/or the need or condition of the patient. More particularly, FIG. 3, (being a longitudinal sectional view therethrough) illustrates said clamp means as comprising a short-length strip 50a of deformable shaperetaining material, such as lead, and a superposed short-length strip 50b of a flexible material having substantial tensile strength, such as metal, plastic or fabric, the ends of said strips being clipped or otherwise affixed one to the other. Said clamp means is applied to the longer leg 36 of the siphon preferably just in advance of the priming bulb 38, the siphon leg being assumed to be formed of material capable of being flattened somewhat. The siphon leg 36 is shown in FIG. 3 as extending through space provided between said strips 50a, 50b with its calibre unchanged.

FIG. 4 illustrates the calibre of the siphon leg decreased, i.e. its bore having been ensmalled, which is simply achieved by bowing the lead strip 50a of said clamp means 50 relatively upwardly so that, rather than extending straightway as in FIG. 3, it assumes an arcuate or bowed configuration as viewed in longitudinal section. Such results in the upper high tensile strip 50b exerting downward pressure on the siphon leg (or tubing) as flattens it, thereby decreasing the calibre thereof in accordance with the degree of bowing applied to the lower lead strip 50a. It will be understood that upon again straightening the lead strip 50a, the upper, high tensile material strip 50b will release its pressure on the siphon leg (or tubing). Thus, there is provided simple, effective means not only for altering the calibre of the fluid-flow opening of the lower end of the siphon leg 36 (or the intravenous tubing itself if said means is placed other than in advance of the priming bulb 38 as illustrated) in accordance with the viscosity of the fluid being administered and/or the need or condition of the patient, but also for effecting same aseptically as follows from the calibre-altering means being entirely enclosed within the deformable-reformable plastic wall reservoir 24.

In operation of a parenteral fluid administration set as described, fluid from the bottle 10 is allowed to flow freely through the fluid outlet leg 18 of the aforesaid adapter 14 and thence collect in the flow-regulator container 16A, whereupon float 30 rides upwardly on the surface thereof, carrying with it the siphon 32 to the position of said parts as indicated in broken lines, FIG. 1, with any excess fluid passing through overflow tube 22 to the lower receiving-reservoir 24 and thence into the intravenous tubing 26 as is necessary to free said tubing of air.

At this point, fluid flow from the reservoir (bottle 10) may be cut off and the intravenous tubing 26 closed to further flow there-through by a clamp valve 42 located near the site of the injection needle, such insuring that the intravenous tubing and the lower third (approximately) of the receiving reservoir 24 is filled with fluid and thus free of air.

The siphon 32 may now be primed so as to render same operative, with priming being achieved by first finger-pinching the tube 40 depending from the priming bulb 38 to close same, and then applying hand-squeeze pressure on the receiving reservoir 24 and simultaneously on said priming bulb 38 to a degree substantially flattening said bulb. Thereupon, while maintaining pinch pressure on said depending tube 40, squeeze pressure on the priming bulb 38 is released and said squeeze and release operations repeated as needed, with the result that fluid is sucked into and through the siphon legs 34, 36 to said bulb. The needle 28 may now be introduced into the patient's vein, following which the clamp valve 42 is rendered inoperative (opened).

Foow of the intravenous fluid from the reservoir (bottle 10) to the container 16A of the flow regulator 16 will of course be adjusted by manual setting of valve 18a to that required to maintain the level of the fluid on which the float 30 rides at the open top 22a of the vertical overflow tube 22.

Fluid flow having now been established, such will be maintained at a constant uniform rate via the floating-siphon action, the nurse or nurses in attendance being now required only to see to it that the fluid level in the flow regulator container 16A is maintained at or near the level of the open top 22a of the overflow tube 22.

Assuming the clamp valve 42 to have been adjusted to a position normally maintaining a body of the fluid in the lower third (approximately) of the receiving reservoir 24, the aforementioned floating sphere 44 will ride on the surface thereof. However, upon the fluid in the reservoir (bottle 10) and the lower end portion of the container 16A being expended (used up), the floating sphere 44 will lower to a position (shown in broken lines) in which it closes off the outlet from the lower tapered end 24a of the receiving reservoir 24, thereby preventing air from entering the patient's vein.

It is to be understood that the herein disclosed invention is not limited to use of a bottle-type reservoir as illustrated, since fluids to be administered intravenously are sometimes supplied in plastic bags, for example. Also, although the invention has been disclosed as a device for insuring a controllable uniform rate of flow of an intravenous fluid from a reservoir (bottle or plastic bag) source of said fluid to a patient via an injection needle, the invention is not so limited, since other uses and applications requiring a controllable uniform rate of flow of a fluid or liquid moving between a reservoir and a point or site of use are intended to be covered by the herein invention.

Having thus disclosed my invention and its uses and advantages, I make the following claims. Therefore I claim:

1. Means for maintaining uniform flow of a parenteral fluid from a reservoir supply thereof through a flow path to a distal point of use, including a flow regulator positioned in said flow path and receiving fluid from said reservoir flowing thereto by gravity, said flow regulator comprising an upright fluid-receiving container, an open-ended tube of substantially lesser axial length than that of said upright container affixed to and extending uprightly from and opening through the container bottom wall, the upper open end of said tube determining the maximum level of fluid collecting in said container, a siphon operatively disposed in said upright container for limited vertical movement therein, said siphon comprising a U-tube having a fluid intake end and a fluid outlet end, said outlet end being vertically below said inlet end and extending through the container bottom wall into a fluid collecting reservoir, the wall structure of said reservoir providing means for aseptically priming the siphon thereby inducing fluid flow therethrough, and means for maintaining constant the vertical distance (a) between the siphon intake and the surface of the fluid in the container and (b) the vertical distance between the siphon intake and the siphon outlet.

2. Means for maintaining uniform flow of a parenteral fluid from a reservoir supply through a flow path according to claim 1, said last means including a float riding on the surface of the fluid in said container and through which the intake end of the siphon U-tube extends and is affixed.

3. Means for maintaining uniform flow of a parenteral fluid from a reservoir supply through a flow path according to claim 2, wherein said float has annular shape and said uprightly disposed open-ended tube projects upwardly and centrally through the opening in said float.

4. Means for maintaining uniform flow of a fluid from a reservoir supply through a flow path according to claim 3, wherein said outlet leg of the siphon extends downwardly through the open-ended tube and terminates in a priming bulb.

5. A parenteral fluid administration set for administering a parenteral fluid intravenously at a controllable uniform flow-rate from comprising a source of said fluid, a flow regulator to which said fluid flows from said source by gravity, said flow regulator comprising an upright fluid-collecting container, an open-ended tube having substantially lesser axial length than the height of said fluid container affixed to and extending uprightly from and opening through the container bottom wall, the upper open end of the tube determining the maximum level of the fluid flowing to and collecting in said container, with any overflow passing downwardly through the tube and collecting in an elongated receiving reservoir affixed to and depending from the bottom-end wall of the aforesaid fluid container, a floating siphon disposed in said container including a float member riding on the surface of the body of fluid collecting in the container and a siphon affixed to said float so as to be movable vertically as one with said float, the shorter leg of the siphon extending downwardly through the float member with its end opening into the fluid on which the float member rides, the longer leg of the siphon extending downwardly through said upright open-ended tube to and with its end opening into a siphon priming bulb disposed in the upper end of the receiving reservoir, means for aseptically priming said siphon including said bulb and means depending therefrom for closing off the lower end of said bulb, the construction and arrangement being such that upon flow being established through the siphon, said floating siphon operates to maintain constant both the vertical distance between the siphon intake and the surface of the fluid in the fluid container and the vertical distance between said siphon intake and the siphon outlet, and tubing means connected to the lower end of the receiving reservoir and extending to an injection needle.

6. A parenteral fluid administration set according to claim 5, wherein said receiving reservoir, said priming bulb and said means depending from said bulb are fashioned from materials capable of being deformed by hand-or finger-squeeze pressure applied against the outer surfaces thereof and to reform to original configuration upon cessation of said pressures.

7. A parenteral fluid administration set according to claim 5 and further including means for aseptically altering the calibre (bore) of the siphon in accordance with the viscosity of the particular parenteral fluid being administered and/or the condition or need of the patient.

8. A parenteral fluid administration set according to claim 7 wherein said calibre - altering means is located in the flow path at a point thereof intermediate the fluid container and the priming bulb.

9. A parenteral fluid administration set according to claim 5, wherein said receiving reservoir has a tapering lower end which opens to said tubing to the injection needle.

10. A parenteral fluid administration set according to claim 9, and further including a floatable sphere having diameter greater than the opening to said tubing. Said sphere normally riding on the surface of fluid collecting in said tapering lower end but lowering to close off said opening upon intravenous fluid from said reservoir supply being expended.

* * * * *